United States Patent
Kim et al.

(10) Patent No.: US 9,953,754 B2
(45) Date of Patent: Apr. 24, 2018

(54) MEDICAL APPARATUS AND METHOD OF OPERATING THE SAME

(71) Applicant: SAMSUNG MEDISON CO., LTD., Gangwon-do (KR)

(72) Inventors: Soon-deok Kim, Gangwon-do (KR); Jung-sik Song, Gangwon-do (KR); Yeon-ho Kim, Gangwon-do (KR); Yu-ri Kim, Gangwon-do (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 299 days.

(21) Appl. No.: 14/644,018

(22) Filed: Mar. 10, 2015

(65) Prior Publication Data
US 2015/0264828 A1 Sep. 17, 2015

Related U.S. Application Data

(60) Provisional application No. 61/951,268, filed on Mar. 11, 2014.

(30) Foreign Application Priority Data

Mar. 24, 2014 (KR) ........................ 10-2014-0034296

(51) Int. Cl.
*H01F 7/06* (2006.01)
*A61B 5/00* (2006.01)
*F16M 11/10* (2006.01)
*F16M 11/18* (2006.01)
*F16M 13/02* (2006.01)

(52) U.S. Cl.
CPC ............... *H01F 7/064* (2013.01); *A61B 5/00* (2013.01); *A61B 5/743* (2013.01); *A61B 5/7475* (2013.01); *F16M 11/10* (2013.01); *F16M 11/18* (2013.01); *F16M 13/02* (2013.01)

(58) Field of Classification Search
CPC ...... Y01T 292/11; Y01T 24/32; G06F 1/1679; G06F 1/1616
USPC ....................................................... 361/147
See application file for complete search history.

(56) References Cited

U.S. PATENT DOCUMENTS

2003/0142080 A1* 7/2003 Uhl ........................ G06F 1/181
345/173
2015/0036060 A1* 2/2015 Yaghoubi ................. B60N 2/01
348/837

FOREIGN PATENT DOCUMENTS

KR 10-2009-0124830 A 12/2009

* cited by examiner

*Primary Examiner* — Dharti Patel
(74) *Attorney, Agent, or Firm* — McDermott Will & Emery LLP

(57) ABSTRACT

Provided are a medical apparatus and a method of operating the same. The medical apparatus includes a body including a user input unit to which a user instruction is input, a display device displaying a medical image and is rotatable about the body, and a locking member setting the display device to be rotatable when the display device is touched and fixes the display device when the display device is not touched.

19 Claims, 10 Drawing Sheets

MEDICAL APPARATUS AND METHOD OF OPERATING THE SAME

RELATED APPLICATIONS

This application claims the benefit of U.S. Provisional Application No. 61/951,268, filed on Mar. 11, 2014, in the US Patent Office and Korean Patent Application No. 10-2014-0034296, filed on Mar. 24, 2014, in the Korean Intellectual Property Office, the disclosures of which are incorporated herein in their entireties by reference.

BACKGROUND

1. Field

One or more exemplary embodiments relate to a medical apparatus and a method of operating the same.

2. Description of the Related Art

As medical apparatuses for obtaining medical images of a physical body, an ultrasound device, a magnetic resonance imaging (MRI) device, a computed tomography (CT) device, an X-ray device, etc., are widely used. These devices may take an image of a part or the whole of a physical body due to the resolution of the image or their sizes. Also, it is possible to take an image of a whole physical body at a time, or to take several images of parts of the physical body and then to obtain a composite image of the whole physical body by composing the taken images.

Such a medical apparatus includes a display device for displaying a medical image, a manipulation panel to which an instruction of a user may be input, etc., and the display device and the manipulation panel are connected to the body of the medical apparatus.

The display device is necessary to be moved and disposed at a convenient position for the user to see.

SUMMARY

One or more exemplary embodiments include a medical apparatus including a rotatable display device, and a method of operating the medical apparatus.

Additional aspects will be set forth in part in the description which follows and, in part, will be apparent from the description, or may be learned by practice of the presented embodiments.

According to one or more exemplary embodiments, a medical apparatus includes a body including a user input unit to which a user instruction is input, a display device displaying a medical image and is rotatable about the body, and a locking member setting the display device to be rotatable when the display device is touched and fixes the display device when the display device is not touched.

The medical apparatus may further include a sensor sensing a touch upon the display device.

The display device may be rotatable up and down or left and right about the body.

The locking member may include a first locking member disposed in the body, and a second locking member disposed in the display device and is attached to and detached from the first locking member.

When the display is touched, the first locking member may be separated from the second locking member, and thus the display device may be rotatable, and when the display is untouched, the first locking member may be attached to the second locking member, and thus the display device may be fixed.

The first locking member and the second locking member may be attached to each other by magnetic force.

One of the first locking member and the second locking member may include a magnet, and a remaining one of the first locking member and the second locking member may include a magnetic material.

One of the first locking member and the second locking member may include a permanent electromagnet.

The medical apparatus may further include a current supplier supplying the permanent electromagnet with current, and a switching unit turning on or off a connection between the current supplier and the permanent electromagnet according to whether or not the display device is touched.

The switching unit may turn off the connection between the current supplier and the permanent electromagnet when the display device is not touched, and may turn on the connection between the current supplier and the permanent electromagnet when the display device is touched.

The first locking member and the second locking member may be disposed apart from each other by restoring force.

The medical apparatus may further include a restoration member generating the restoring force corresponding to a movement of the first locking member.

The restoration member may generate the restoring force when the first locking member is moved and attached to the second locking member, and may restore the first locking member to an original position by the restoring force when the first locking member is detached from the second locking member.

A direction of the restoring force may be normal to a rotation direction of the display device.

According to one or more exemplary embodiments, a method of operating a medical apparatus including a body and a display device connected to the body by a hinge includes sensing a touch upon the display device; setting, when the display device is sensed to be untouched, the display device to a fixed mode in which the display device is fixed; and setting, when the display device is sensed to be touched, the display device to a rotation mode in which the display device rotatable.

The setting of the display device to the fixed mode may include attaching a first locking member disposed in the body to a second locking member disposed in the display device. The setting of the display device to the rotation mode may include detaching the first locking member from the second locking member.

The first locking member and the second locking member may be attached to each other by magnetic force.

One of the first locking member and the second locking member may include a permanent electromagnet, and a remaining one of the first locking member and the second locking member may include a conductive material.

When the display is sensed to be untouched, the permanent electromagnet may be supplied with no current, and when the display is sensed to be touched, the permanent electromagnet may be supplied with current.

The setting of the display device to the fixed mode may include having a restoring force corresponding to a movement of the first locking member generated by a restoring member, and the setting of the display device to the rotation mode may include restoring the first locking member to an original position by the restoring force.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
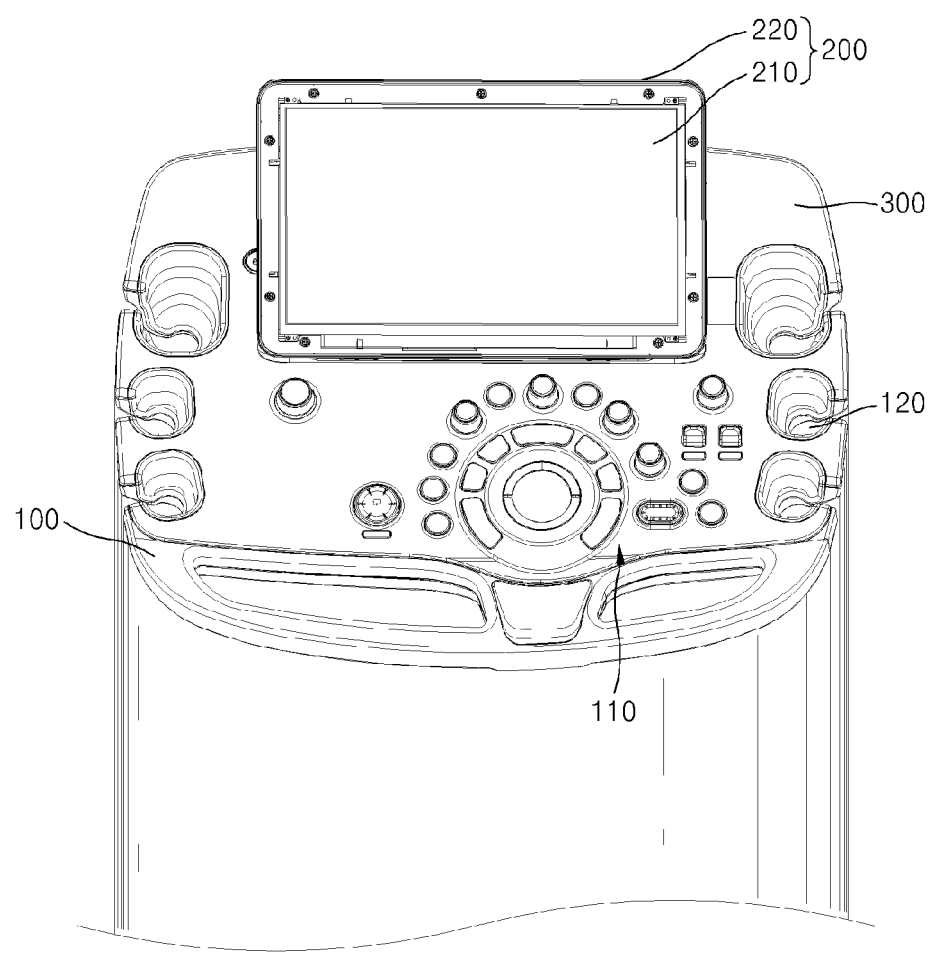
FIG. 1A is a front view of an ultrasound diagnostic device as a medical apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Through the specification, an "object" may include a person or an animal, or a part of a person or an animal. For example, the object may include an organ, such as the liver, the heart, the womb, the brain, the breast, the abdomen, etc., or a blood vessel. In addition, a "user" refers to a medical professional, such as a doctor, a nurse, a clinical pathologist, or a medical image expert, or an engineer who repairs a medical apparatus, but the user is not limited thereto.

Figure 1B:
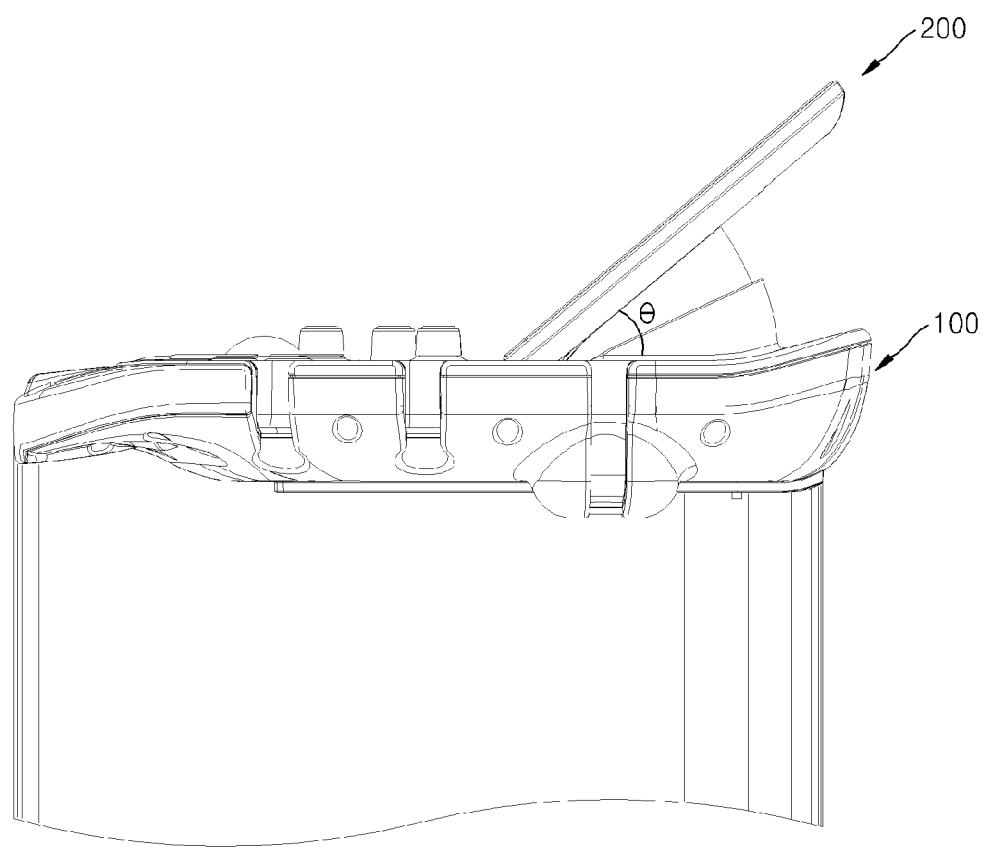
FIG. 1B is a side view of the ultrasound diagnostic device of FIG. 1A.

FIG. 1A is a front view of an ultrasound diagnostic device as a medical apparatus 10 according to an embodiment, and FIG. 1B is a side view of the ultrasound diagnostic device of FIG. 1A. FIGS. 1A and 1B show the ultrasound diagnostic device as the medical apparatus 10. However, the medical apparatus 10 is not limited to an ultrasound diagnostic device, and may be applied to various medical apparatuses such as an X-ray imaging apparatus.

As shown in FIGS. 1A and 1B, the ultrasound diagnostic device that is an example of the medical apparatus 10 may include a body 100 that includes a user input unit 110 to which an instruction of a user is input, a display device 200 that displays a medical image and is installed in the body 100, and an ultrasound probe (not shown) that emits ultrasound waves to an object and receives ultrasound echoes from the object. Through a cable and a connector connected with the ultrasound probe in one body, the ultrasound probe may be connected to the body 100 or perform wireless communication with the body 100. The body 100 may further include a probe holder 120 for fixing the ultrasound probe. Although not shown in the drawings, the body 100 may a signal processor that generates an ultrasound image by processing ultrasound data received from the ultrasound probe. In addition, circuit elements necessary for the ultrasound diagnostic device to operate are disposed in the body 100. When the ultrasound probe is physically separated from the body 100, the medical apparatus according to an embodiment may be limited to the body 100 including the user input unit 110 and the display device 200.

The user input unit 110 is a means for a user to input data for controlling the medical apparatus 10. The user input unit 110 may include a keypad, a touch panel, a trackball, and so on. The user input unit 110 is not limited to this configuration, and may further include various input means such as a jog wheel and a jog switch.

The display device 200 displays information processed in the medical apparatus 10. For example, the display device 200 may display an ultrasound image generated by the signal processor (not shown) in the body 100, and may also display a graphic user interface (GUI) for requesting an input of a user.

The display device 200 may include at least one of a liquid crystal display (LCD), a thin film transistor (TFT)-LCD, an organic light-emitting diode (OLED) display, a flexible display, a three-dimensional (3D) display, and an electrophoretic display.

The display device 200 may include a display unit 210 that displays medical images and a user interface, and a housing 220 that gives the appearance of the display device 200. In addition, the display device 200 may further include a connection unit (not shown) that connects the display device 200 and the body 100. The connection unit will be described later. The display unit 210 may be disposed on the front surface of the display device 200.

The display device 200 may be disposed to be tilted by a predetermined angle with respect to the body 100. Also, the angle between the display device 200 and the body 100 is adjusted for the convenience of a user. A structure and method for adjusting the angle between the display device 200 and the body 100 will be described below.

Figure 2A:
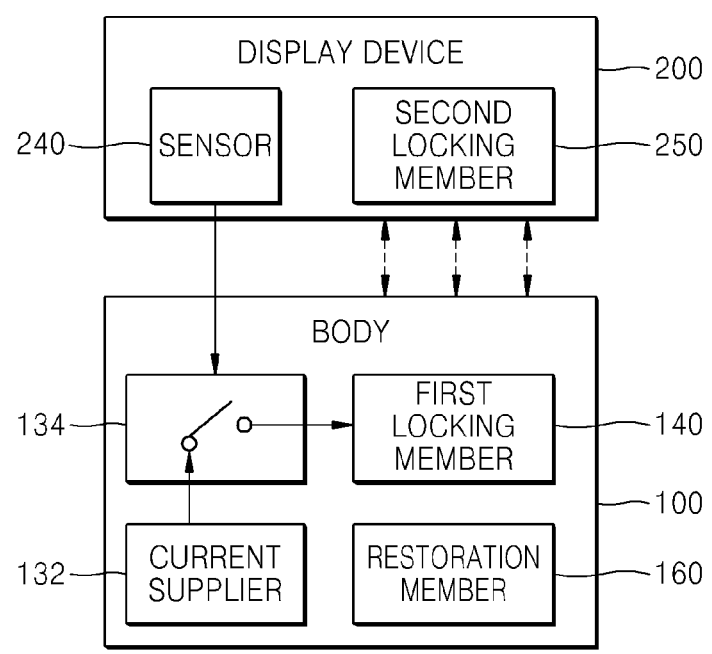
FIG. 2A is a block diagram of a medical apparatus that adjusts the angle between a display device and a body.
Figure 2B:
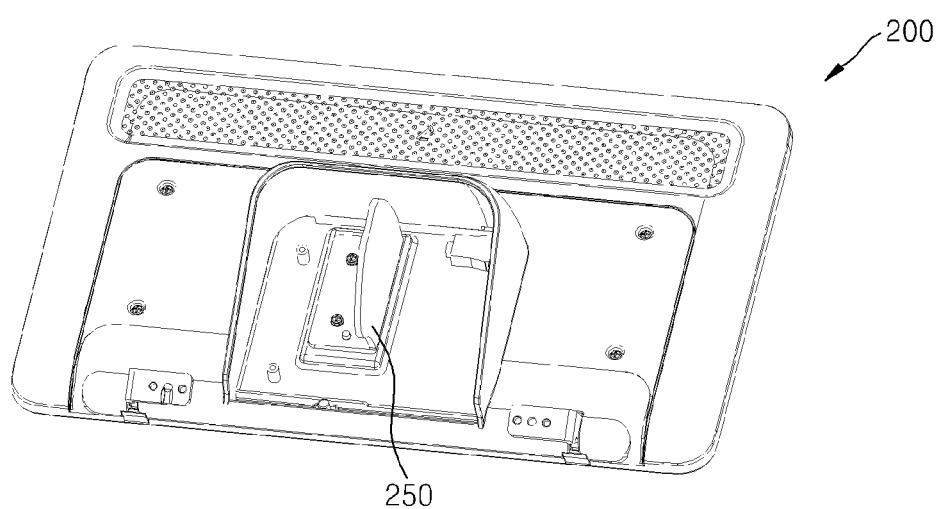
FIG. 2B shows the appearance of a display device of FIG. 1B.
Figure 2C:
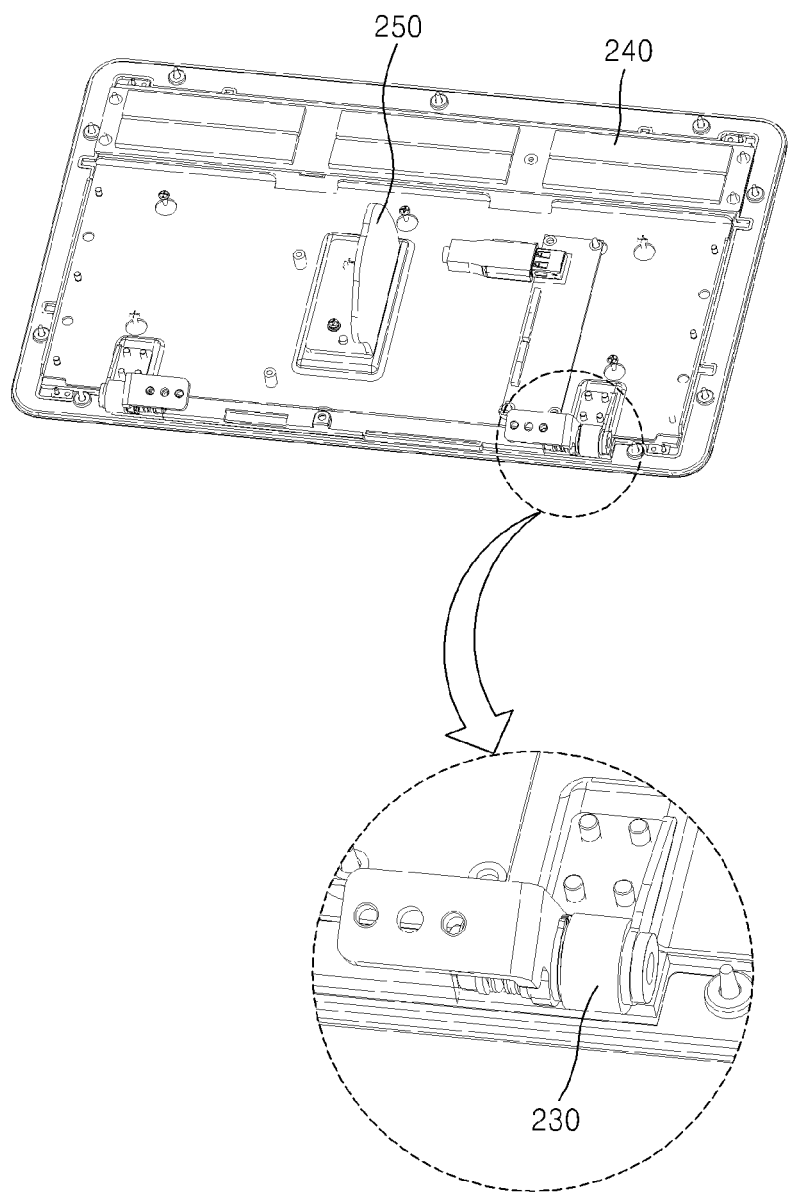
FIG. 2C shows the display device of FIG. 2B from which a housing is removed.
Figure 2D:
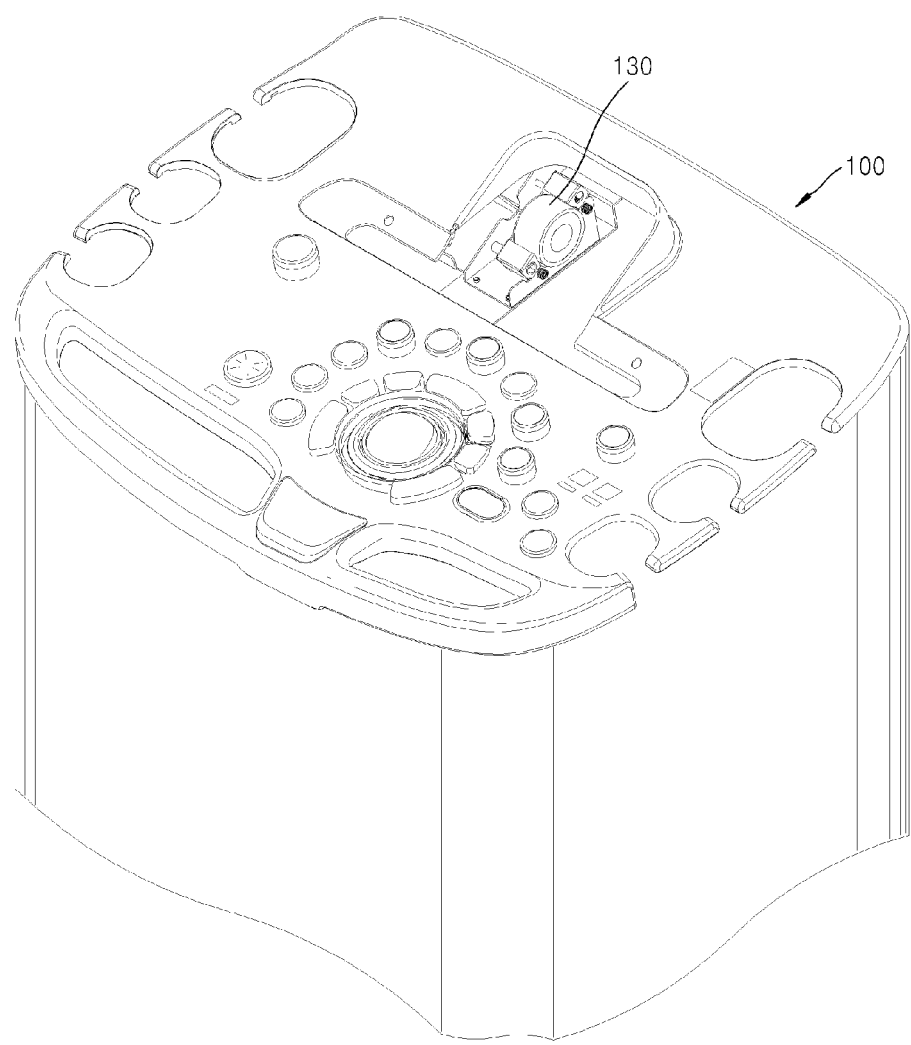
FIG. 2D shows a body of FIG. 1A from which the display device is removed.
Figure 2E:
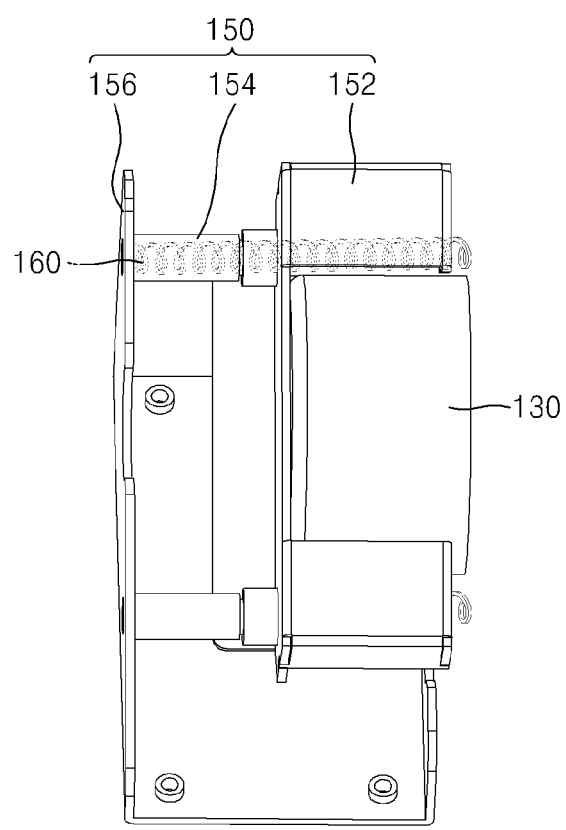
FIG. 2E is an enlarged view of a first locking member and a support member of FIG. 2D.
Figure 3A:
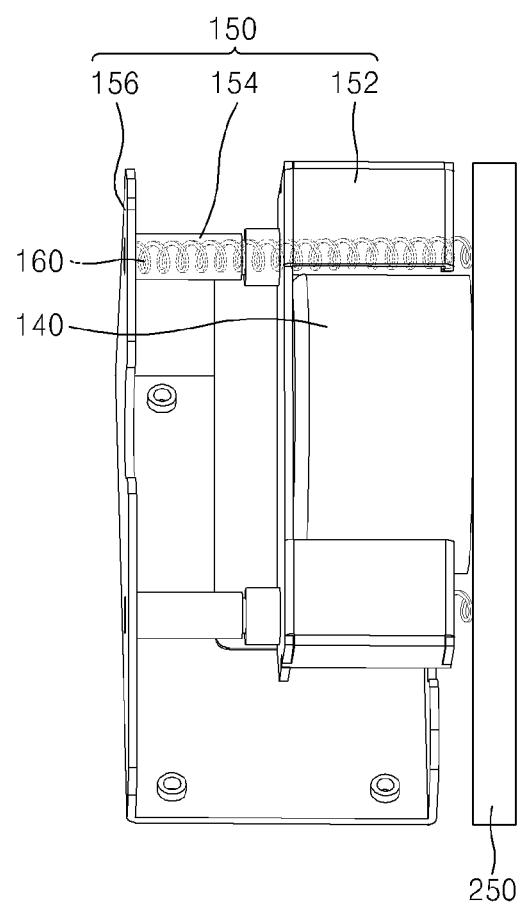
FIG. 3A shows a state in which the first locking member and the support member are attached to each other.
Figure 3B:
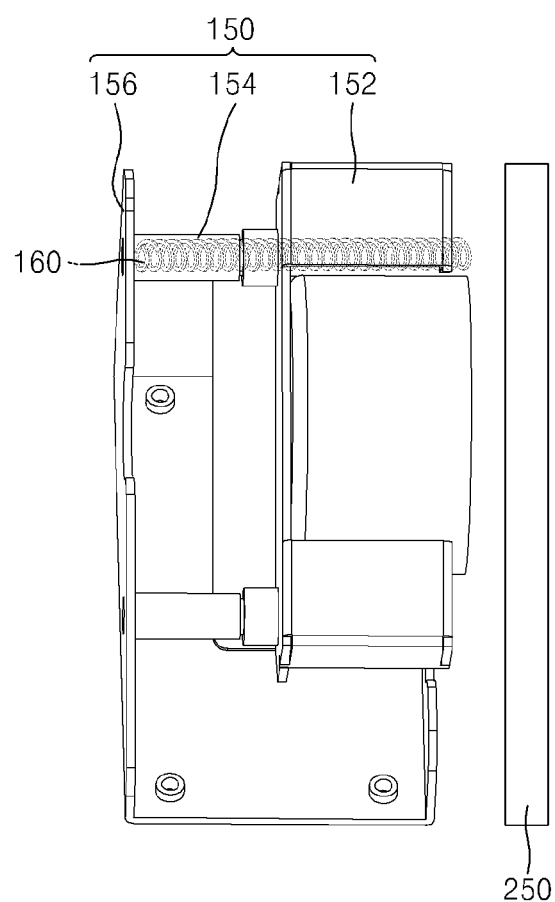
FIG. 3B shows a state in which the first locking member and the support member are separated from each other.

FIG. 2A is a block diagram of a medical apparatus that adjusts the angle between the display device 200 and the body 100, FIG. 2B shows the appearance of the display device 200 of FIG. 1B, FIG. 2C shows the display device 200 of FIG. 2B from which a housing is removed, FIG. 2D shows the body 100 of FIG. 1A from which the display device 200 is removed, and FIG. 2E is an enlarged view of a first locking member 140 and a support member 150. Also, FIG. 3A shows a state in which the first locking member 140 and a second locking member 250 are attached to each other, and FIG. 3B shows a state in which the first locking member 140 and the second locking member 250 are separated from each other.

As shown in FIGS. 2A to 3B, the display device 200 of the medical apparatus 10 is connected to the body 100 by a hinge 230, and may rotate. The display device 200 may rotate about a hinge axis.

The medical apparatus 10 may further include a sensor 240 that is disposed in the display device 200 and senses whether or not the display device 200 is touched, and a controller 130 that controls whether or not to rotate the display device 200 according to whether or not the display device 200 is touched.

The sensor 240 is a sensor that senses a touch of a user upon the display device 200, and may be a touch sensor. The touch sensor may be implemented as various types of touch sensors, such as a capacitive overlay type, a resistive overlay type, an infrared beam type, a surface acoustic wave (SAW) type, an integral strain gauge type, a piezoelectric type, and so on. The sensor 240 may be disposed on a rear surface of the display device 200. The sensor 240 may be disposed in an upper area of the rear surface of the display device 200. Therefore, when a user grabs the upper area of the display device 200, the sensor 240 may sense a touch of the user. The position at which the sensor 240 is disposed is not limited to the upper area of the rear surface of the display device 200. The display device 200 may be disposed in any area of the display device 200 as long as it is possible to sense whether or not a user grabs the display device 200. For example, a touch sensor present in the display unit 210 of the display device 200 may be used as a sensor according to an embodiment.

According to a sensing result of the sensor 240, the controller 130 may set the display device 200 to a rotation mode in which the display device 200 may rotate or a fixed mode in which the display device 200 is fixed. For example, the controller 130 may set the display device 200 to the rotation mode when the display device 200 is touched, and to the fixed mode when the display device 200 is not touched.

When the display device 200 is set to the rotation mode, the user may rotate the display device 200 while grabbing the display device 200, thereby adjusting an angle θ between the display device 200 and the body 100. On the other hand, when the display device 200 is set to the fixed mode, the angle θ between the display device 200 and the body 100 may be fixed.

In order for the display device 200 to be set to the fixed mode or the rotation mode as described above, the medical apparatus 10 may further include the first locking member 140 disposed in the body 100 and the second locking member 250 disposed in the display device 200 and attached to and detached from the first locking member 140. The first locking member 140 may be disposed on the body 100 that faces the display device 200, for example, the upper surface. The second locking member 250 may be disposed on the display device 200 that faces the body 100, for example, the lower surface. Therefore, when the first locking member 140 is attached to the second locking member 250, the medical apparatus 10 enters the fixed mode, and the angle θ between the display device 200 and the body 100 is fixed. Also, when the second locking member 250 is separated from the first locking member 140, the medical apparatus 10 enters the rotation mode, and the angle θ between the display device 200 and the body 100 may be adjusted according to a motion of a user.

The first locking member 140 and the second locking member 250 may be attached to each other by magnetic force. For example, the first locking member 140 may include a magnet, and the second locking member 250 may include a magnetic material. In particular, the first locking member 140 may be a permanent electromagnet that has magnetism according to whether or not current is supplied.

For example, the controller 130 may include a current supplier 132 that supplies the first locking member 140 with current, and a switching unit 134 that supplies or does not supply the first locking member 140 with the current of the current supplier 132 according to a result received from the sensor 240. When a result indicating that the display device 200 has been touched is received from the sensor 240, the switching unit is turned on and supplies the first locking member 140 with the current. On the other hand, when a result indicating that the display device 200 has not been touched is received from the sensor 240, the switching unit is turned off and does not supply the first locking member 140 with the current.

When the first locking member 140 is supplied with no current, the first locking member 140 has magnetism and thus may be attached to the second locking member 250. On the other hand, when the first locking member 140 is supplied with the current, the first locking member 140 lose its magnetism and thus may be detached from the second locking member 250.

The permanent electromagnet that is the first locking member 140 may have a cylindrical shape, and the second locking member 250 may have a plate shape. Besides the shapes shown in the drawings, the first locking member 140 and the second locking member 250 may have various shapes. The rotation range of the display device 200 may be a range in which at least partial areas of the first locking member 140 and the second locking member 250 overlap.

Meanwhile, the support member 150 that is attached to the body 100 and supports the first locking member 140 may be further disposed in the body 100, and a restoration member 160 that generates restoring force corresponding to a movement of the first locking member 140 may be further disposed in the body 100.

The support member 150 may include a bracket 152 having a groove therein in which the first locking member 140 is installed, a shaft 154 that has one end in contact with the bracket 152 and guides the bracket 152 to have a straight-line motion, and a bracket housing 156 that fixes the shaft 154 in the body 100. At least a part of the restoration member 160 may be disposed in the shaft 154. The restoration member 160 may include, for example, a spring. Therefore, when the first locking member 140 is moved toward the second locking member 250 and attached to the second locking member 250 by magnetic force, restoring force may be generated by the restoration member 160. When the first locking member 140 lose its magnetism, the first locking member 140 may be restored to its original position by the restoring force of the restoration member 160, so that the first locking member 140 and the second locking member 250 may be spaced apart from each other. The direction of the restoring force may be parallel to a movement direction of the first locking member 140 and normal to a rotation direction of the display device 200. Since the direction of the restoring force is normal to the rotation direction of the display device 200, it is possible to reduce the influence of rotation of the display device 200 upon the restoring force as much as possible.

In an embodiment, it has been described that the restoration member 160 is interposed between the support member 150 and the first locking member 140. Since the first locking member 140 is spaced apart from the second locking member 250 due to the restoration member 160, no friction occurs between the first locking member 140 and the second locking member 250 when a user rotates the display device 200. Therefore, the user may easily rotate the display device 200. However, the exemplary embodiments are not limited to this configuration. When almost no friction occurs between contact surfaces of the first locking member 140 and the second locking member 250, the restoration member 160 and the support member 150 may be unnecessary.

In an embodiment, it has been described that the permanent electromagnet is disposed in the body 100 and a conductive material is disposed in the display device 200, but exemplary embodiments are not limited to this configuration. The permanent electromagnet may be disposed in the display device 200, and the magnetic material may be disposed in the body 100. Accordingly, the support member 150 and the restoration member 160 may also be disposed in the display device 200.

In addition, it has been described that the permanent electromagnet is restored to its original position by restoring force, but exemplary embodiments are not limited to this configuration. It is also possible to form a structure in which the second locking member 250 may be restored to its original position by restoring force. Furthermore, it has been described that the controller 130 is disposed in the body 100, but exemplary embodiments are not limited to this configuration. The controller 130 may be disposed in the display device 200.

Figure 4:
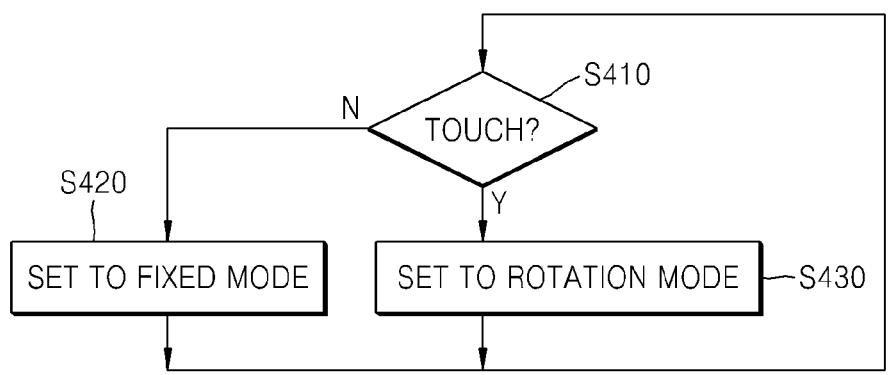
FIG. 4 is a flowchart of a method of operating a medical apparatus with a touch of a user according to an embodiment.

FIG. 4 is a flowchart of a method of operating the medical apparatus 10 with a touch of a user according to an embodiment.

Referring to FIG. 4, in the medical apparatus 10 including the body 100 and the display device 200 connected to the body 100 by the hinge 230, the sensor 240 senses a touch upon the display device 200 (operation 410). The sensor 240 is disposed in an area of the display device 200, and may be disposed in an area that may be grabbed by a user. A sensing result of the sensor 240 may be applied to the controller 130 of the medical apparatus 10. The controller 130 may be formed in the body 100 as a circuit element.

When the display device 200 is sensed to be untouched (operation 410—N), the controller 130 may set the display device 200 to the fixed mode in which the display device 200 is fixed (operation 420). The first locking member 140 may be disposed in the body 100, and the second locking member 250 may be disposed in the display device 200. When the first locking member 140 is attached to the second locking member 250, the display device 200 may be set to the fixed mode. The first locking member 140 and the second locking member 250 may be attached to each other by magnetic force. For example, the first locking member 140 may include a permanent electromagnet that has magnetism according to whether or not current is supplied, and the second locking member 250 may include a magnetic material. Then, when the display device 200 is sensed to be untouched, the permanent electromagnet is supplied with no current. Therefore, the permanent electromagnet has magnetism and thus may be attached to the second locking member 250. In order for the first locking member 140 to be attached to the second locking member 250, the first locking member 140 may move toward the second locking member 250. Due to the movement of the first locking member 140, restoring force may be generated by the restoration member 160.

When the display device 200 is sensed to be touched (operation 410—Y), the controller 130 may set the display device 200 to the rotation mode in which the display device 200 may rotate (operation 430). When the first locking member 140 is separated from the second locking member 250, the display device 200 may be set to the rotation mode. For example, when the display device 200 is sensed to be touched, the current supplier 132 supplies the permanent electromagnet with current, so that the permanent electromagnet loses its magnetism. Then, the first locking member 140 may be detached from the second locking member 250. Also, the first locking member 140 may be restored to its original position by the restoring force of the restoration member 160.

As described above, according to the one or more of the above exemplary embodiments, since it is possible to set the display device 200 to the fixed mode or the rotation mode with only a touch of a user, no additional manipulation unit for fixing or rotating the display device 200 is necessary, so that the convenience of a user may be improved. The display device 200 is set to the rotation mode by a touch upon the display device 200, so that the convenience of a user is further improved. Also, the display device 200 may be fixed by a user's operation of finishing a touch upon the display device 200, and thus no additional manipulation is necessary.

As described above, a display device may rotate up and down by adjusting an angle between the display device and a body, but the rotation of the display device is not limited thereto. The display device may rotate to left and right about the body by adjusting the angle. In this case, whether the display device rotates up and down or to left and right about the body may be determined according to a structure of a hinge.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A medical apparatus comprising:
   a body comprising a user input unit to which a user instruction is input;
   a display device displaying a medical image and is rotatable relative to the body;
   a sensor sensing a touch upon the display device;
   a locking member setting the display device to be rotatable when the sensor senses the display device is touched and fixes the display device when the sensor senses the display device is not touched; and
   a current supplier which supplies the locking member with current,
   wherein, when the sensor senses the touch, the current supplier supplies the locking member with current so that the display device is rotatable, and, when the sensor does not sense the touch, the current supplier supplies the locking member with no current so that the display device is fixed.

2. The medical apparatus of claim 1, wherein the display device is rotatable up and down or left and right about the body.

3. The medical apparatus of claim 1, wherein the locking member comprises:
   a first locking member disposed in the body; and
   a second locking member disposed in the display device and is attached to and detached from the first locking member.

4. The medical apparatus of claim 3, wherein when the display device is touched, the first locking member is separated from the second locking member, and thus the display device is rotatable, and
   when the display device is untouched, the first locking member is attached to the second locking member, and thus the display device is fixed.

5. The medical apparatus of claim 4, wherein one of the first locking member and the second locking member comprises a magnet, and
   a remaining one of the first locking member and the second locking member comprises a magnetic material.

6. The medical apparatus of claim 5, wherein one of the first locking member and the second locking member comprises a permanent electromagnet.

7. The medical apparatus of claim 6, further comprising:
a switching unit turning on or off a connection between the current supplier and the permanent electromagnet according to whether or not the display device is touched.

8. The medical apparatus of claim 7, wherein the switching unit turns off the connection between the current supplier and the permanent electromagnet when the display device is not touched, and turns on the connection between the current supplier and the permanent electromagnet when the display device is touched.

9. The medical apparatus of claim 3, wherein the first locking member and the second locking member are attached to each other by magnetic force.

10. The medical apparatus of claim 3, wherein the first locking member and the second locking member are disposed apart from each other by restoring force.

11. The medical apparatus of claim 10, further comprising a restoration member generating the restoring force corresponding to a movement of the first locking member.

12. The medical apparatus of claim 11, wherein the restoration member generates the restoring force when the first locking member is moved and attached to the second locking member, and restores the first locking member to an original position by the restoring force when the first locking member is detached from the second locking member.

13. The medical apparatus of claim 10, wherein a direction of the restoring force is normal to a rotation direction of the display device.

14. A method of operating a medical apparatus comprising a body and a display device connected to the body by a hinge, the method comprising:
sensing a touch upon the display device via a sensor;
setting, when the display device is sensed by the sensor to be untouched, by a locking member to which current is supplied, the display device to a fixed mode in which the display device is fixed; and
setting, when the display device is sensed by the sensor to be touched, by a locking member to which no current is supplied, the display device to a rotation mode in which the display device is rotatable.

15. The method of claim 14, wherein the setting of the display device to the fixed mode comprises attaching a first locking member of the locking member disposed in the body to a second locking member of the locking member disposed in the display device, and
the setting of the display device to the rotation mode comprises detaching the first locking member from the second locking member.

16. The method of claim 15, wherein the setting of the display device to the fixed mode comprises having a restoring force corresponding to a movement of the first locking member generated by a restoring member, and
the setting of the display device to the rotation mode comprises restoring the first locking member to an original position by the restoring force.

17. The method of claim 14, wherein the first locking member and the second locking member are attached to each other by magnetic force.

18. The method of claim 14, wherein one of the first locking member and the second locking member comprises a permanent electromagnet, and
a remaining one of the first locking member and the second locking member comprises a conductive material.

19. The method of claim 18, wherein when the display device is sensed to be untouched, the permanent electromagnet is supplied with no current, and
when the display device is sensed to be touched, the permanent electromagnet is supplied with current.

* * * * *